(12) United States Patent
Farascioni

(10) Patent No.: US 7,997,468 B2
(45) Date of Patent: Aug. 16, 2011

(54) SURGICAL INSTRUMENT WITH CLAMP

(75) Inventor: David Farascioni, Bethel, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 249 days.

(21) Appl. No.: 12/430,193

(22) Filed: Apr. 27, 2009

(65) Prior Publication Data

US 2009/0272784 A1 Nov. 5, 2009

Related U.S. Application Data

(60) Provisional application No. 61/050,282, filed on May 5, 2008.

(51) Int. Cl.
*A61B 17/068* (2006.01)

(52) U.S. Cl. ........... 227/176.1; 227/19; 227/180.1; 606/139; 606/219

(58) Field of Classification Search ............... 227/19, 227/176.1, 175.1, 180.1, 178.1
See application file for complete search history.

(56) References Cited

U.S. PATENT DOCUMENTS

| | | | |
|---|---|---|---|
| 2,511,382 A | 6/1950 | Stonehouse | |
| 4,216,891 A | 8/1980 | Behike | |
| 4,273,281 A | 6/1981 | Smith et al. | |
| 4,881,545 A | 11/1989 | Isaacs et al. | |
| 5,071,052 A | 12/1991 | Rodak et al. | |
| 5,389,098 A | 2/1995 | Tsuruta et al. | |
| 5,403,326 A | 4/1995 | Harrison et al. | |
| 5,571,116 A | 11/1996 | Bolanos et al. | |
| 5,582,611 A | 12/1996 | Tsuruta et al. | |
| 5,655,698 A | 8/1997 | Yoon | |
| 5,662,259 A | 9/1997 | Yoon | |
| 5,676,674 A | 10/1997 | Bolanos et al. | |
| 5,782,397 A | 7/1998 | Koukline | |
| 5,868,760 A * | 2/1999 | McGuckin, Jr. | 606/139 |
| 5,897,562 A * | 4/1999 | Bolanos et al. | 606/139 |
| 5,928,264 A | 7/1999 | Sugarbaker et al. | |
| 6,086,600 A | 7/2000 | Kortenbach et al. | |
| 6,126,058 A * | 10/2000 | Adams et al. | 227/180.1 |
| 6,312,437 B1 | 11/2001 | Kortenbach | |
| 6,494,888 B1 | 12/2002 | Laufer et al. | |

(Continued)

FOREIGN PATENT DOCUMENTS

EP 1621139 A 2/2006

(Continued)

OTHER PUBLICATIONS

European Search Report for corresponding EP 10 25 0934, date of completion is Aug. 19, 2010 (3 pages).

(Continued)

*Primary Examiner* — Scott A. Smith

(57) ABSTRACT

A surgical instrument for surgically joining tissue is disclosed. The surgical instrument includes a handle portion, an endoscopic portion, a pair of jaw members and a clamp. The endoscopic portion extends distally from the handle portion and defines a first longitudinal axis. The pair of jaw members is disposed adjacent a distal end of the endoscopic portion and extends generally distally therefrom. At least one of the jaw members is movable with respect to the other between an open position and an approximated position for engaging body tissue therebetween. The clamp is disposed adjacent the jaw members and extends generally distally from the endoscopic portion. The clamp is movable between an open position and an approximated position for engaging body tissue. The clamp is independently movable with respect to the jaw members.

19 Claims, 8 Drawing Sheets

U.S. PATENT DOCUMENTS

| | | | |
|---|---|---|---|
| 6,544,271 B1 * | 4/2003 | Adams et al. ................. | 606/139 |
| 6,551,328 B2 | 4/2003 | Kortenbach | |
| 6,558,400 B2 | 5/2003 | Deem et al. | |
| 6,601,749 B2 * | 8/2003 | Sullivan et al. ............ | 227/180.1 |
| 6,663,640 B2 | 12/2003 | Kortenbach | |
| 6,695,198 B2 * | 2/2004 | Adams et al. ............. | 227/175.1 |
| 6,821,285 B2 | 11/2004 | Laufer et al. | |
| 6,835,199 B2 | 12/2004 | McGuckin, Jr. et al. | |
| 6,874,669 B2 * | 4/2005 | Adams et al. ............. | 227/175.1 |
| 6,974,453 B2 | 12/2005 | Woloszko et al. | |
| 6,981,979 B2 * | 1/2006 | Nicolo .......................... | 606/153 |
| 6,997,931 B2 | 2/2006 | Sauer et al. | |
| 7,083,630 B2 | 8/2006 | DeVries et al. | |
| 7,097,650 B2 | 8/2006 | Weller et al. | |
| 7,207,472 B2 * | 4/2007 | Wukusick et al. ......... | 227/181.1 |
| 7,401,721 B2 * | 7/2008 | Holsten et al. ............. | 227/176.1 |
| 7,543,730 B1 | 6/2009 | Marczyk | |
| 2002/0078967 A1 | 6/2002 | Sixto, Jr. et al. | |
| 2003/0120285 A1 | 6/2003 | Kortenbach | |
| 2004/0006351 A1 | 1/2004 | Gannoe et al. | |
| 2004/0010271 A1 | 1/2004 | Kortenbach | |
| 2004/0087976 A1 | 5/2004 | DeVries et al. | |
| 2004/0215216 A1 | 10/2004 | Gannoe et al. | |
| 2005/0149072 A1 | 7/2005 | DeFries et al. | |
| 2005/0177176 A1 | 8/2005 | Gerbi et al. | |
| 2005/0203547 A1 | 9/2005 | Weller et al. | |
| 2005/0203548 A1 | 9/2005 | Weller et al. | |
| 2005/0256533 A1 | 11/2005 | Roth et al. | |
| 2006/0106288 A1 | 5/2006 | Roth et al. | |
| 2006/0116697 A1 | 6/2006 | Carter et al. | |
| 2006/0116698 A1 | 6/2006 | Bayne et al. | |
| 2006/0122462 A1 | 6/2006 | Roth | |
| 2006/0149316 A1 | 7/2006 | DeVries et al. | |
| 2006/0151568 A1 | 7/2006 | Weller et al. | |
| 2006/0163312 A1 | 7/2006 | Viola et al. | |
| 2006/0190018 A1 | 8/2006 | Baker et al. | |
| 2006/0241661 A1 | 10/2006 | DeVries et al. | |
| 2006/0271076 A1 | 11/2006 | Weller et al. | |
| 2007/0005082 A1 | 1/2007 | Kraemer et al. | |
| 2007/0088373 A1 | 4/2007 | Baker | |
| 2007/0095877 A1 | 5/2007 | Racenet et al. | |
| 2007/0112363 A1 | 5/2007 | Adams | |
| 2007/0112364 A1 | 5/2007 | Gerbi et al. | |
| 2007/0162056 A1 | 7/2007 | Gerbi et al. | |
| 2007/0167960 A1 | 7/2007 | Roth et al. | |
| 2007/0167963 A1 | 7/2007 | Beem et al. | |
| 2007/0187456 A1 | 8/2007 | Viola et al. | |
| 2007/0233161 A1 | 10/2007 | Weller et al. | |
| 2007/0250083 A1 | 10/2007 | Deem et al. | |
| 2008/0078800 A1 | 4/2008 | Hess et al. | |

FOREIGN PATENT DOCUMENTS

| | | |
|---|---|---|
| EP | 1 782 743 | 5/2007 |
| EP | 1908414 A | 4/2008 |
| EP | 1 935 354 A2 | 6/2008 |
| EP | 1 550 411 B1 | 7/2009 |
| GB | 2029754 | 3/1980 |
| WO | WO 94/18893 | 9/1994 |
| WO | WO 01/89440 | 11/2001 |
| WO | WO 02/05721 | 1/2002 |
| WO | WO 02/30296 | 4/2002 |
| WO | WO 2006/055385 | 5/2006 |

OTHER PUBLICATIONS

European Search Report EP 09251240 dated Oct. 5, 2009. (8 pages).
European Search Report for EP 09252246.5-1269 date of completion is Nov. 24, 2009 (3 pages).
European Search Report for 09251237.5 dated Jun. 17, 2009 (4 pages).
European Search Report for Application No. 09251420.7 dated Sep. 7, 2009. (2 pages).

* cited by examiner

SURGICAL INSTRUMENT WITH CLAMP

CROSS-REFERENCE TO RELATED APPLICATIONS

The present application claims the benefit of and priority to U.S. Provisional Patent Application Ser. No. 61/050,282 filed on May 5, 2008, the entire contents of which being herein incorporated by reference in its entirety.

BACKGROUND

1. Technical Field

The present disclosure relates generally to instruments for surgically joining tissue and, more specifically, to a surgical instrument having a clamp.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Other examples of a surgical instrument of the present disclosure include electrosurgical (e.g., monopolar and bipolar) forceps. Electrosurgical forceps utilize both mechanical clamping action and electrical energy to affect hemostasis by heating the tissue and blood vessels to coagulate, cauterize and/or seal tissue.

SUMMARY

The present disclosure relates to a surgical instrument for surgically joining tissue. The surgical instrument includes a handle portion, an elongated portion, a pair of jaw members and a clamp. The elongated portion extends distally from the handle portion and defines a first longitudinal axis. The pair of jaw members is disposed adjacent a distal end of the elongated portion. At least one of the jaw members is movable with respect to the other between an open position and an approximated position for engaging body tissue therebetween. The clamp is disposed adjacent the jaw members and extends generally distally from the elongated portion. The clamp is movable between an open position and an approximated position for engaging body tissue. The clamp is independently movable with respect to the jaw members.

In a disclosed embodiment, the clamp includes a first portion and a second portion and at least one portion of the clamp is pivotable with respect to the other portion about a pivot point disposed at a proximal portion of the clamp. In another disclosed embodiment, each of the jaw members is substantially parallel to the clamp.

In embodiments of the surgical instrument, the jaw members include an anvil assembly and a cartridge assembly, or are configured to deliver electrosurgical energy to tissue. In disclosed embodiments, the jaw members are curved with respect to the first longitudinal axis and/or the clamp is curved with respect to the first longitudinal axis. In further disclosed embodiments, the jaw members are rotatable with respect to the handle portion, about the first longitudinal axis.

In a disclosed embodiment, the jaw members are part of a loading unit and the loading unit is attachable to the elongated portion.

In an embodiment, the end effector defines a second longitudinal axis. Here, the end effector is movable from a first position where the second longitudinal axis is substantially aligned with the first longitudinal axis to at least a second position where the second longitudinal axis is disposed at an angle to the first longitudinal axis.

The present disclosure also relates to a loading unit configured for releasable engagement with a surgical instrument. The loading unit includes a body portion, a pair of jaw members, and a clamp. The body portion defines a first longitudinal axis. A proximal portion of the body portion is configured for releasable engagement with an elongated portion of the surgical instrument. The pair of jaw members is disposed distally of the body portion. At least one of the jaw members is movable with respect to the other between an open position and an approximated position for engaging body tissue therebetween. The clamp is disposed adjacent the jaw members and is movable between an open position and an approximated position for engaging body tissue. The clamp is independently movable with respect to the jaw members.

In a disclosed embodiment, the clamp of the loading unit includes a first portion and a second portion and at least one portion of the clamp is pivotable with respect to the other portion about a pivot point disposed at a proximal portion of the clamp.

In an embodiment, each of the jaw members is substantially parallel to the clamp. Embodiments of the loading unit also include jaw members that include an anvil assembly and a cartridge assembly or jaw members that are configured to deliver electrosurgical energy to tissue. Embodiments also include jaw members that are curved with respect to the first longitudinal axis and/or a clamp that is curved with respect to the first longitudinal axis.

The present disclosure also relates to a loading unit configured for releasable engagement with a surgical instrument, the loading unit including a pair of jaw members, and a clamp, and being configured for releasable engagement with an elongated portion of the surgical instrument. At least one of the jaw members is movable with respect to the other between an open position and an approximated position for engaging body tissue therebetween. The clamp is disposed adjacent the jaw members and is movable between an open position and an approximated position for engaging body tissue. The loading unit has a first mechanism for actuating the jaw members and a closing mechanism for the clamp.

In certain embodiments, the closing mechanism includes a clamp link. The clamp link may extend proximally to engage an instrument link on the surgical instrument upon engagement of the loading unit with the elongated portion of the surgical instrument. In certain embodiments, the first mechanism is arranged to move the jaw members between the open and approximated positions of the jaw members. In another embodiment, the first mechanism is arranged to fire staples from at least one of the jaw members.

The present disclosure also relates to a surgical instrument for joining tissue where the surgical instrument includes a handle portion, an elongated portion extending distally from the handle portion and defining a longitudinal axis, a pair of jaw members disposed adjacent a distal end of the endoscopic portion, at least one of the jaw members being movable with respect to the other of the jaw members between an open position and an approximated position for engaging body tissue therebetween, and a clamp disposed adjacent the jaw members and being movable between an open position and an approximated position for engaging body tissue, the jaw members being curved.

In certain embodiments, the jaw members are curved and have a convex side and a concave side, the clamp being disposed adjacent the concave side of the jaw members. The clamp may be curved or have a shape that corresponds to the curved jaw members.

The present disclosure also relates to a method of surgically joining tissue. The method includes the steps of providing a surgical instrument, moving a clamp of the surgical instrument from an open position towards an approximated position to engage body tissue, moving at least one of the jaw members of the surgical instrument with respect to the other from an open position towards an approximated position to engage body tissue, and actuating the jaw members to join tissue. The surgical instrument used in the disclosed method includes a handle portion, an elongated portion, a pair of jaw members and a clamp. The elongated portion extends distally from the handle portion. The pair of jaw members is disposed adjacent a distal end of the elongated portion and at least one of the jaw members is movable with respect to the other between an open position and an approximated position for engaging body tissue therebetween. The clamp is disposed adjacent the jaw members. The clamp is independently movable with respect to the jaw members.

Embodiments of the surgical instrument used in the disclosed method include jaw members having a cartridge assembly and an anvil assembly. Other embodiments of the surgical instrument used in the disclosed method include jaw members that are configured to deliver electrosurgical energy to tissue.

Embodiments of the disclosed method include identifying a portion of intestinal tissue to be joined, the intestinal tissue having an interior, clamping intestinal tissue adjacent the identified portion of intestinal tissue with a clamp of a surgical instrument, washing out or otherwise cleansing the interior of the intestinal tissue so as to include the identified portion of intestinal tissue, approximating jaw members of the surgical instrument to engage the identified portion of intestinal tissue, the jaw members being disposed adjacent the clamp on the surgical instrument, firing staples from at least one of the jaw members.

In certain embodiments, the tissue is joined by delivering ultrasonic or electrosurgical energy to the tissue. After being joined, the tissue may be cut using a blade disposed on the surgical instrument, or disposed on a separate instrument.

In a further aspect a surgical instrument for surgically joining tissue comprises a handle portion; an endoscopic portion extending distally from the handle portion and defining a longitudinal axis; and a pair of jaw members disposed adjacent a distal end of the endoscopic portion. At least one of the jaw members is movable with respect to the other between an open position and an approximated position for engaging body tissue therebetween. The pair of jaw members is curved with respect to the longitudinal axis, the pair of jaw members comprising an anvil assembly and a cartridge assembly. The cartridge assembly houses a plurality of surgical staples arranged to be ejected toward the anvil assembly. A clamp is disposed adjacent the pair of jaw members, the clamp being movable between an open position and an approximated position for engaging body tissue, and the clamp being curved with respect to the longitudinal axis.

In certain embodiments, the clamp is disposed alongside a concave side of the pair of jaws.

The surgical instrument may have surgical staples that are ejected in a direction transverse to the longitudinal axis. The clamp, in certain embodiments, includes a first portion and a second portion, and wherein at least one portion of the clamp is pivotable with respect to the other portion about a pivot point disposed at a proximal portion of the clamp. In the surgical instrument, each of the pair of jaw members can be substantially parallel to the clamp.

In certain embodiments, the pair of jaw members extends linearly along the longitudinal axis. The pair of jaw members can be configured to deliver electrosurgical energy to tissue.

BRIEF DESCRIPTION OF FIGURES

Various embodiments of the presently disclosed surgical instrument are disclosed herein with reference to the drawings, wherein.

DETAILED DESCRIPTION

Figure 1A:
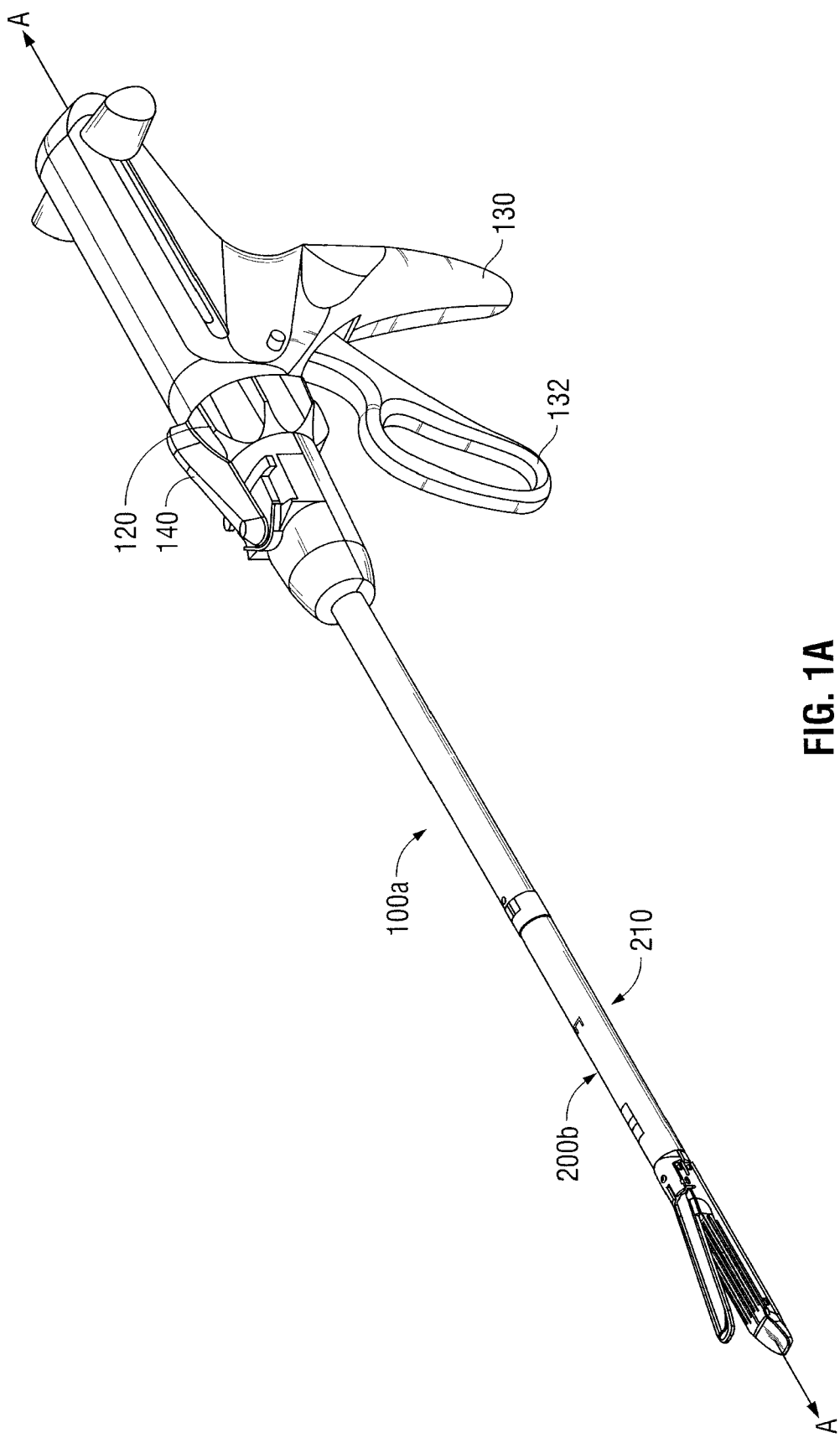
FIG. 1A is a perspective view of a surgical stapling instrument in accordance with the present disclosure.

Embodiments of the presently disclosed surgical instrument, and loading unit for use therewith, are described in detail with reference to the drawings, wherein like reference numerals designate corresponding elements in each of the several views.

A surgical stapling instrument of the present disclosure is indicated as reference numeral 100a in FIG. 1A. An electrosurgical forceps of the present disclosure is indicated as reference numeral 100b in FIG. 1B. Collectively, surgical instruments 100a and 100b are referred to herein as reference numeral 100. Similarly, several features that are common to both surgical stapling instrument 100a and electrosurgical forceps 100b are collectively referred to as the same reference number (e.g., endoscopic portion 110, jaw members 220 and clamp 230).

Figure 1B:
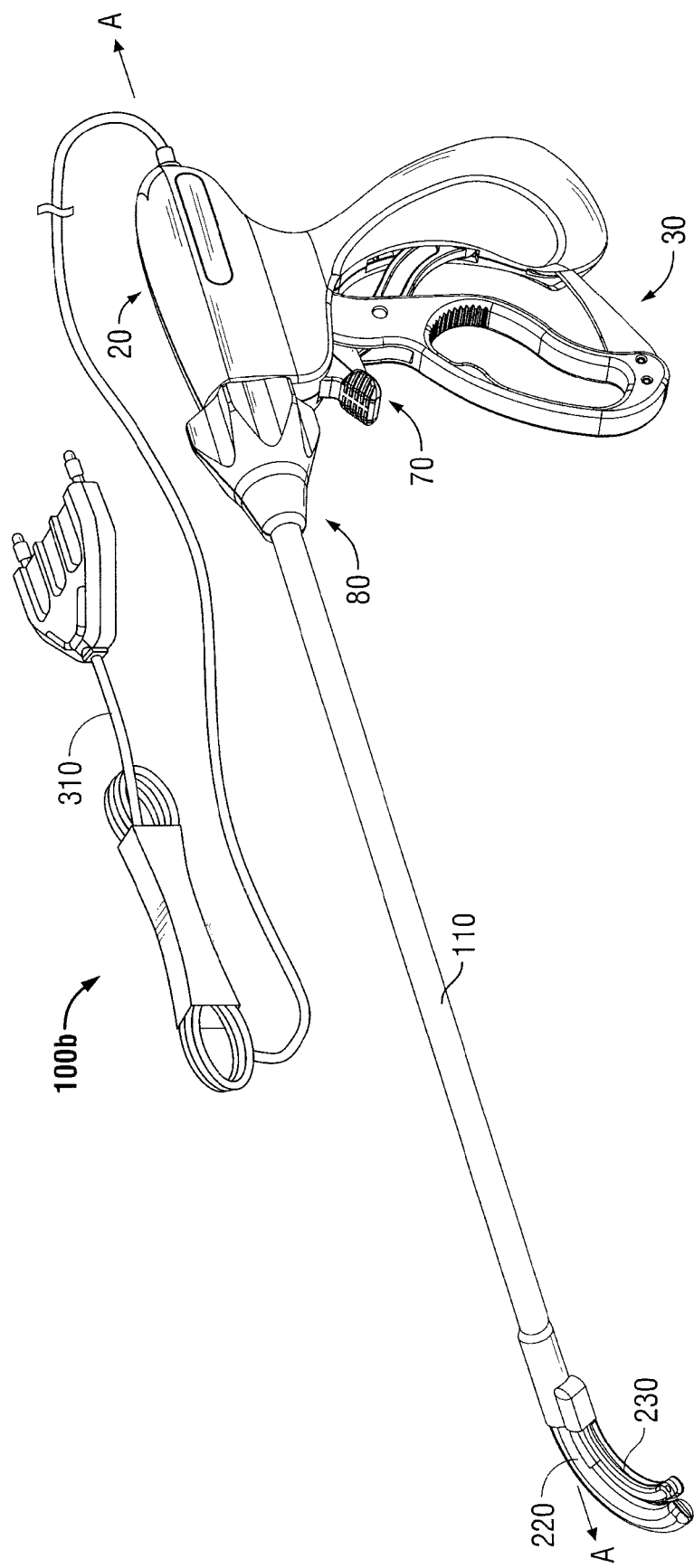
FIG. 1B is a perspective view of an electrosurgical forceps in accordance with the present disclosure.

A loading unit (or "DLU") 200a for use with surgical instrument 100 is shown in FIGS. 2-9. DLU 200a is attachable to an elongated or endoscopic portion 110 of surgical instrument 100, e.g., to allow surgical instrument 100 to have greater versatility. DLU 200a may be configured for a single use, and/or may be configured to be used more than once. Surgical stapling instrument 100a illustrated in FIG. 1A is shown with a different DLU 200b for illustrative purposes. Electrosurgical forceps 100b illustrated in FIG. 1B is shown without a DLU, in accordance with an embodiment of the present disclosure.

Examples of loading units for use with a surgical stapling instrument are disclosed in commonly-owned U.S. Pat. No. 5,752,644 to Bolanos et al., the entire contents of which are hereby incorporated by reference herein. Further details of an endoscopic surgical stapling instrument are described in detail in commonly-owned U.S. Pat. No. 6,953,139 to Milliman et al., the entire contents of which are hereby incorporated by reference herein. Further details of electrosurgical forceps are described in commonly-owned patent application Ser. No. 10/369,894, filed on Feb. 20, 2003, entitled VESSEL SEALER AND DIVIDER AND METHOD OF MANUFACTURING THE SAME, the entire contents of which are hereby incorporated by reference herein.

Referring now to FIGS. 2-9, DLU 200a of the present disclosure is shown. DLU 200a includes a proximal portion 210, a pair of jaw members 220, and a clamp 230. Proximal portion 210 is configured to removably attach to the elongated portion or endoscopic portion 110 of surgical instrument 100 (see FIG. 1A) using a variety of attachment features, such as, for example, a bayonet coupling, latch, detent or snap-fit.

The present disclosure also relates to a surgical instrument 100 having a distal portion that includes the features shown in FIGS. 2-9, where the distal portion (including jaw members 220 and clamp 230) is fixedly attached to the endoscopic portion (i.e., not part of a DLU). Accordingly, the features of the DLU described herein may also be included on surgical stapling instrument 100a and/or electrosurgical forceps 100b without a removable or replaceable loading unit.

Figure 2:
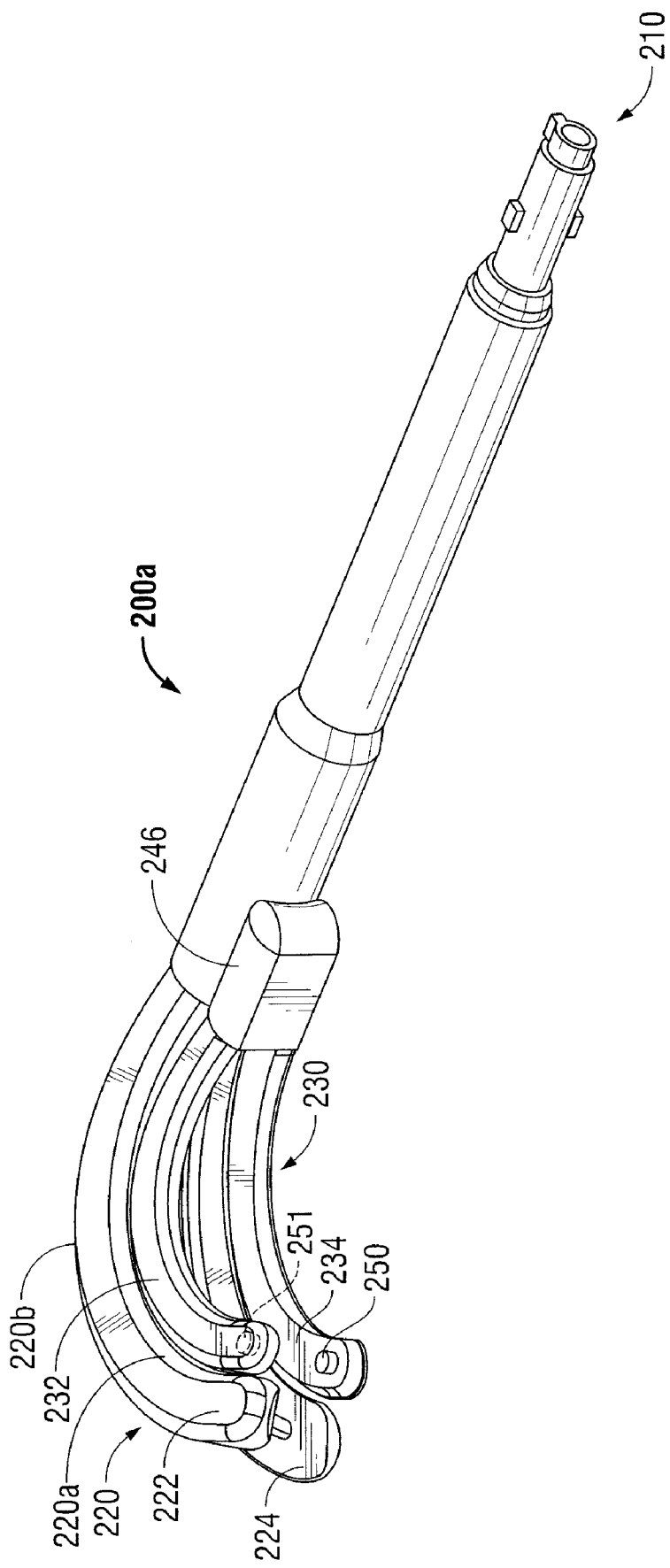
FIGS. 2-4 are perspective views of a loading unit, at various stages of operation, for use with the surgical instruments of FIGS. 1A and 1B.

When used in connection with surgical stapling instrument 100a, the jaw members 220 include a cartridge assembly 222 and an anvil assembly 224 (cartridge assembly and anvil assembly are shown with reference numbers in FIG. 2 for illustrative purposes, but can be in opposite positions than shown without departing from the scope of this disclosure). Cartridge assembly houses a plurality of staples or fasteners (not explicitly shown in the embodiments of FIGS. 2-9). Cartridge assembly 222 includes a plurality of staple pushers for ejecting the staples therefrom. The DLU may include a plurality of cam bars for interacting with the pushers to deploy the surgical fasteners. For example, the apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together. In another example, the apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the channel that supports the cartridge as the drive beam travels distally, to deploy the staples and clamp the anvil and cartridge together. In each of the foregoing examples of surgical fastener and/or staple deployment and formation, the staples are driven in a direction transverse to the longitudinal axis of the endoscopic shaft or endoscopic portion of the apparatus, in a direction toward staple forming pockets or recesses of an anvil assembly.

Anvil assembly 224 includes staple pockets (not explicitly shown in the embodiments of FIGS. 2-9) that are configured to form the staples as they are driven from cartridge assembly 222. A clamp 230 is mounted adjacent cartridge assembly 222 and anvil assembly 224 and is movable with respect to proximal portion 210 to clamp tissue. Clamp 230 includes a first portion 232 and a second portion 234 (see FIG. 5). At least one of first portion 232 and second portion 234 of clamp 230 is movable with respect to the other.

When used in connection with electrosurgical forceps 100b, the jaw members 220 mutually cooperate to grasp, seal and, in some cases, divide tubular vessels and vascular tissues. Electrosurgical forceps 100b is usable with various electrosurgical procedures and generally includes a housing 20, a handle assembly 30, a rotating assembly 80, a trigger assembly 70, and jaw members 220. Electrosurgical forceps 100b also includes a clamp 230 adjacent its jaw members 220 to clamp the vessel or tissue prior to approximating the jaw members and prior to delivering energy thereto. Additionally, electrosurgical forceps 100b includes an electrosurgical cable 310 that connects the electrosurgical forceps 100b to a source of electrosurgical energy, e.g., a generator.

With specific reference to FIGS. 2-6 and 8, jaw members 220 are curved relative to a longitudinal axis A-A defined by endoscopic portion 110 (FIGS. 1A and 1B). As shown, the jaw members 220 of this embodiment extend generally distally from the endoscopic portion. It is envisioned that curved jaw members 200 may facilitate performing certain types of surgical procedures. For example, curved jaw members 200, as compared to straight jaw members (such as the jaw members illustrated in FIG. 1A), may help facilitate access to lower pelvis regions, e.g., during lower anterior resection ("LAR"). Additionally, the inclusion of curved jaw members 220 may allow increased visualization to a surgical site and may also allow more room for a surgeon to manipulate target tissue or the jaw members 220 themselves with his or her hand. It is desirable that clamp 230 is also curved, or that clamp 230 and jaws 220 are parallel in the sense that clamp 230 and jaws 220 do not converge or diverge from each other. As shown in FIG. 2, the jaw members 220 have a concave side 220a and a convex side 220b. The clamp 230 is curved or shaped to correspond to the jaw members 220. The clamp is disposed adjacent the concave side 220a of the jaw members 220. In other embodiments, the clamp is disposed on the convex side 220b of the jaw members. Other shapes for the jaw members and clamp may be used to improve accessibility in the body, such as angled jaw members and/or clamp. To allow even more flexibility in positioning jaw members 220 and clamp 230 (e.g., within lower pelvis regions), surgical instrument 100 may include a rotation feature (e.g., a rotation dial 120 in FIG. 1A or rotating assembly 80 in FIG. 1B) to help enable rotation of jaw members 220 and clamp 230 with respect to a handle portion of surgical instrument 100.

In a surgical stapling instrument in accordance with the present disclosure, a rod or other member is moved distally, through operation of the handle, to actuate the DLU and deploy the staples. For example, referring back to FIG. 1A, at least a partial actuation of movable handle 132 with respect stationary handle 130 translates a drive beam (not explicitly shown in the illustrated embodiments) longitudinally to approximate at least one jaw member with respect to the other. Additionally, at least a partial actuation (e.g., continued actuation) of movable handle 132 translates a firing rod (not explicitly shown in the illustrated embodiments) longitudinally to eject surgical fasteners (e.g., staples) from cartridge assembly 170 and/or to advance a knife to cut tissue. It is also envisioned that first handle approximates the jaw members with respect to one another and actuation of a second handle and/or a third handle causes the ejection of fasteners and advancement of the knife. Other types of handles can be used such as, for example, motor-driven, hydraulic, ratcheting, etc.

With continued reference to FIG. 1A, a lever 140 is shown adjacent rotation dial 120 and may be used to facilitate articulation of the jaw members 220. Actuation of lever 140 causes the jaw members 220 to move between a first position, where the jaw members 220 are substantially aligned with the longitudinal axis A-A, and a second position, where the jaw members 220 are disposed at an angle with respect to the longitudinal axis A-A. It is envisioned that moving lever 140 causes an articulation link to move longitudinally, which results in a proximal portion of at least one jaw member moving proximally or distally. That is, moving the lever 140 in a first direction causes the articulation link to move proximally (which articulates the jaw members 220 in a first direction) and moving the lever 140 in a second, opposite direction causes the articulation link to move distally (which articulates the jaw members 220 in a second direction).

Clamp 230 is shown in FIGS. 2-9. In a disclosed embodiment, clamp 230 is used to compress tissue between first portion 232 and second portion 234 thereof. It is envisioned that a user may position clamp 230 on a proximal side of jaw members 220 (and subsequent staple line or seal line), which may facilitate rectal washout.

Figure 3:
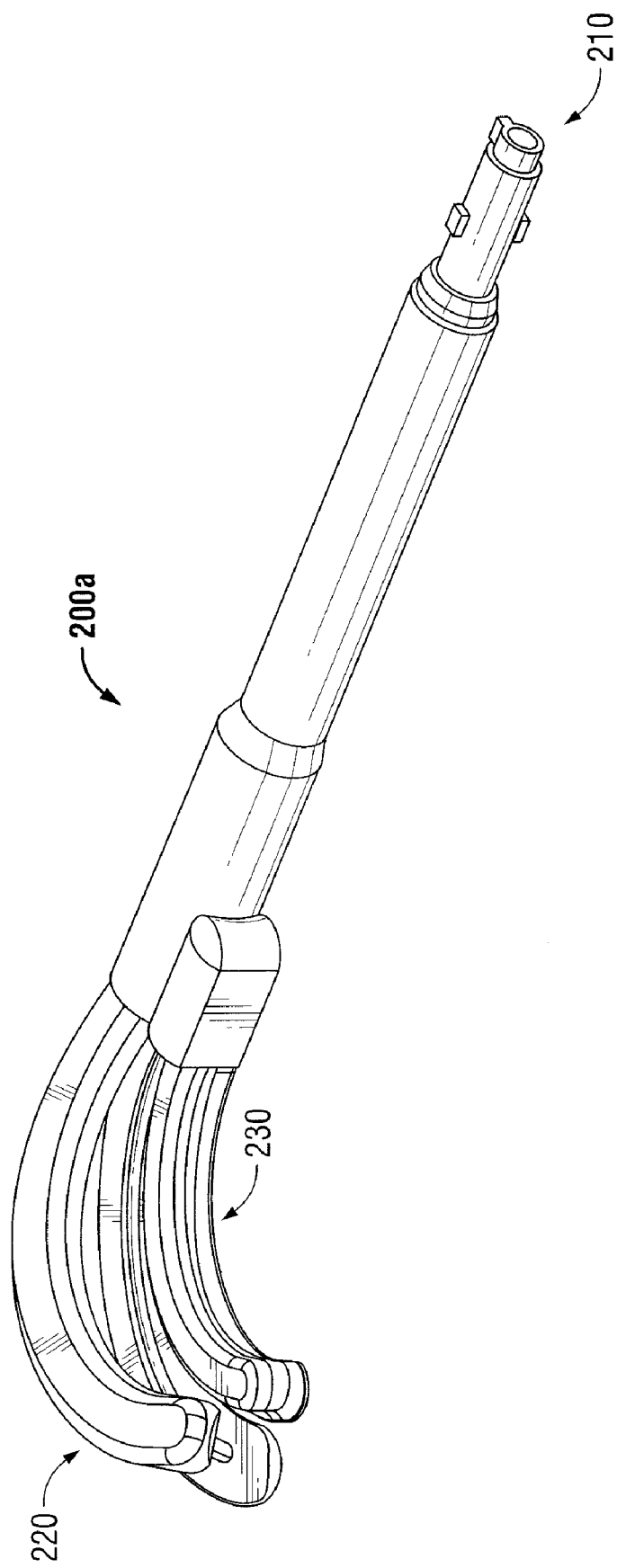
Figure 4:
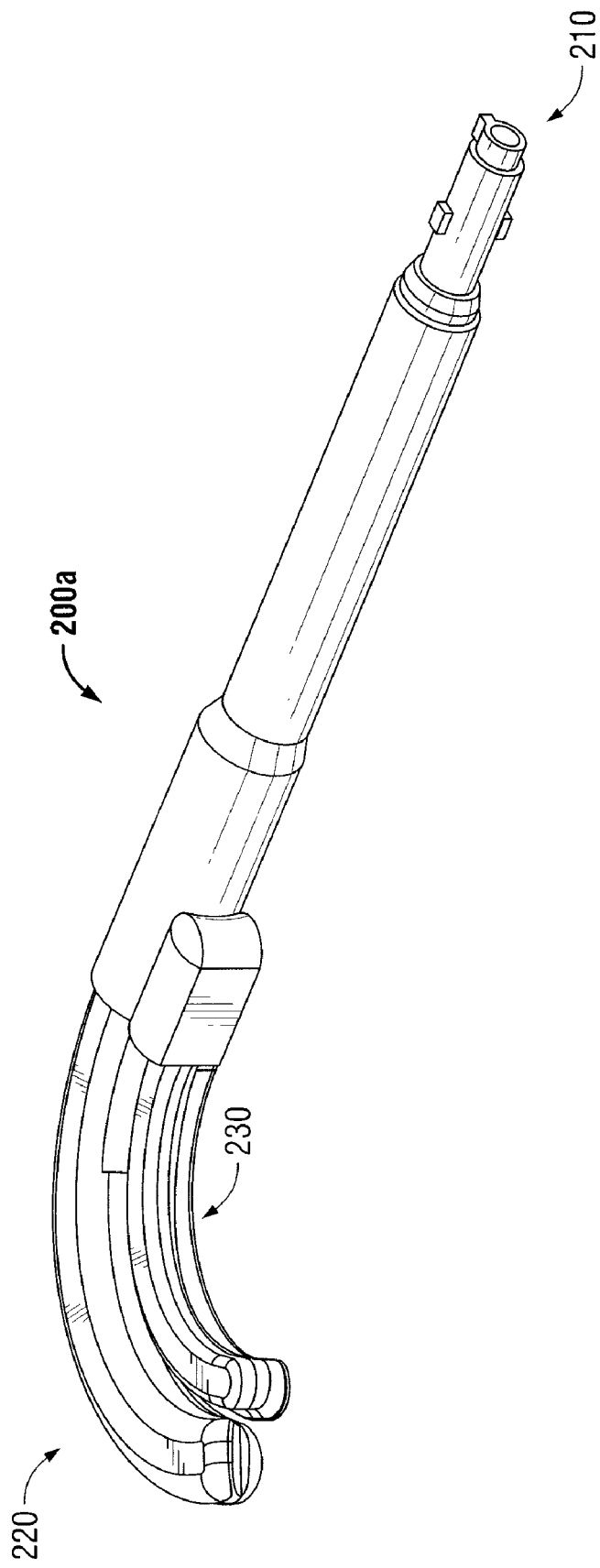

As shown in FIGS. 2-4, a user actuates clamp 230 separately from actuating jaw members 220. In a contemplated use in connection with surgical stapling instrument 100*a*, a user first positions DLU 200*a* about tissue (with clamp 230 and jaw members 220 in an open position, as shown in FIG. 2). Next, the user causes clamp 230 to compress the tissue (FIG. 3) and subsequently closes the jaw members 220 (FIG. 4). After the jaw members 220 are closed in a desired position, the user may then staple tissue (e.g., sequentially) and/or cut tissue.

In a contemplated use in connection with electrosurgical forceps 100*b*, a user first positions jaw members 220 about tissue (with clamp 230 and jaw members 220 in an open position as shown in FIG. 2). Next, the user causes clamp 230 to compress (FIG. 3) and subsequently closes the jaw members 220 (FIG. 4). After the jaw members 220 are closed in a desired position, the user may then depress trigger assembly 70 to deliver energy to the tissue to seal or coagulate the tissue. The user may cut tissue during the sealing/coagulation or thereafter.

As can be appreciated, there are several ways the various actuations of surgical instrument 100 can be achieved. For example, surgical instrument 100 may include a stationary handle, a clamp handle, first movable handle, a second movable handle and a release button. It is further envisioned that a release button can be actuated to release clamp 230 (e.g., from a locked position). One or more movable handles are provided on the surgical instrument 100 to affect closure of clamp 230, closure of the jaw members 220, and firing of staples or delivering energy to tissue.

Other methods of actuating the surgical instrument 100 are also envisioned. For example, when DLU 200*a* is used with surgical stapling instrument 100*a* of FIG. 1*a*, actuation of movable handle 132 may close jaw members 220, fire staples and/or cut tissue, and actuation of lever 140 can be used to operate clamp 230. Additionally, handle portion 130 may include a single movable handle that may be squeezed multiple times, where each actuation can perform a distinct operation. That is, a first actuation of the movable handle may actuate clamp 230, a second actuation of the movable handle may approximate the jaw members 220, and a third actuation of the same movable handle may deploy staples and/or a knife or may deliver energy to the tissue.

Figure 5:
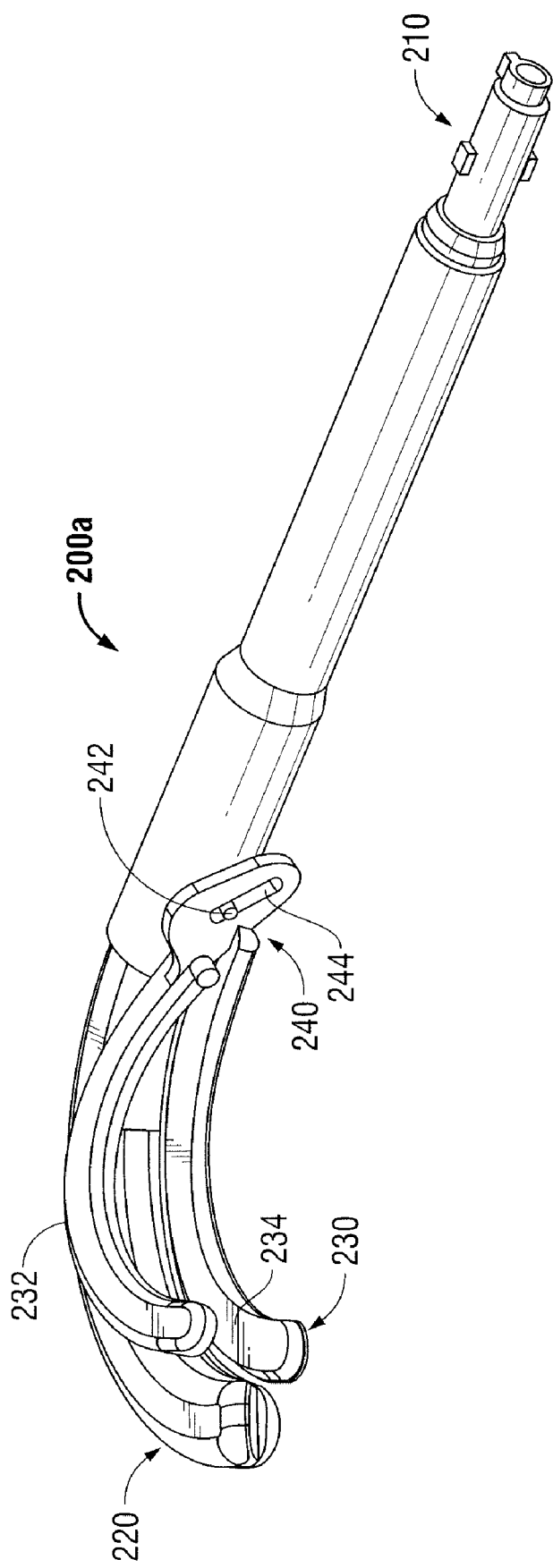
FIGS. 5 and 6 are perspective views of the loading unit of FIGS. 2-4, illustrating a closing mechanism for use with a clamp.
Figure 6:
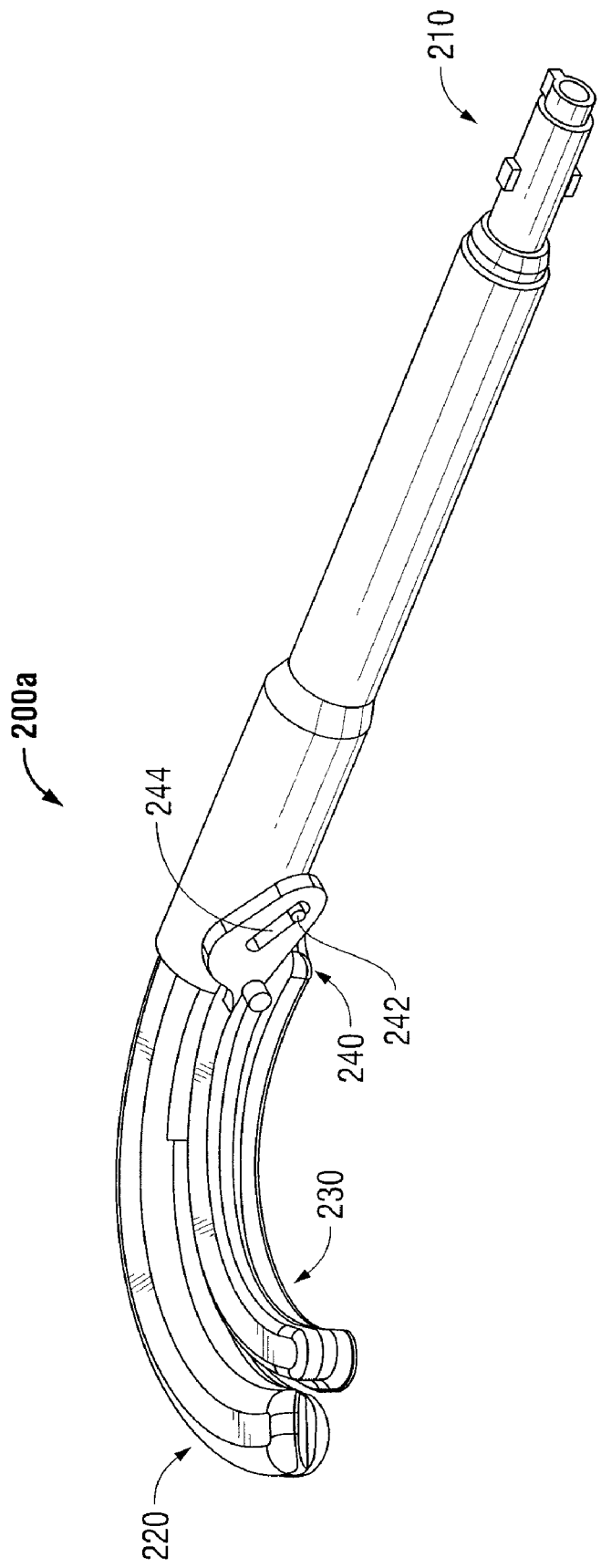
Figure 7:
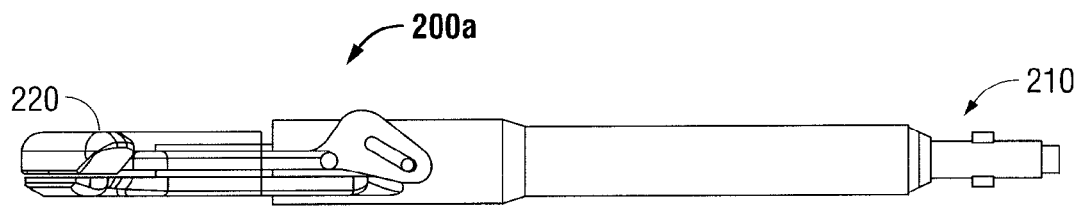
FIG. 7 is a side view of the loading unit of FIGS. 5 and 6.
Figure 8:
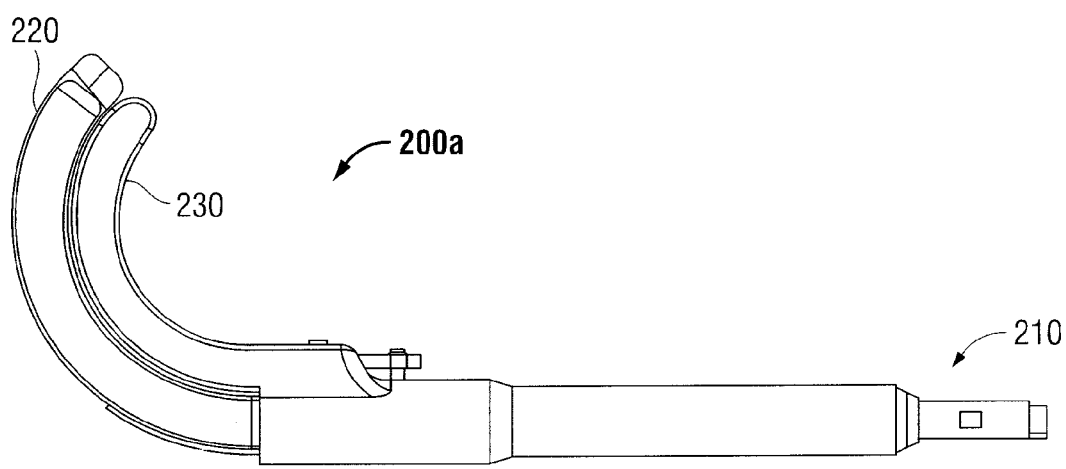
FIG. 8 is a bottom view of the loading unit of FIGS. 5-7.
Figure 9:
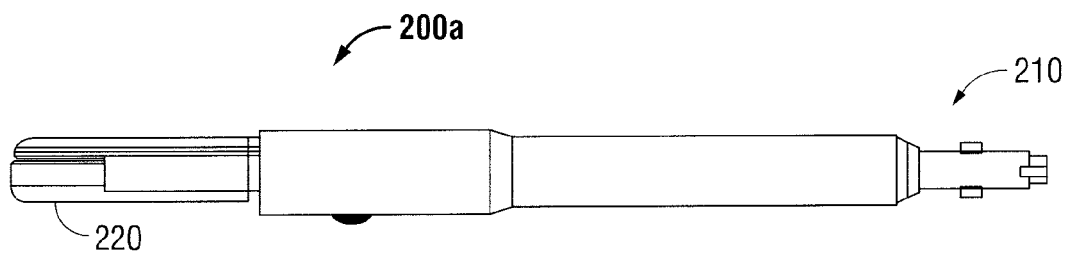
FIG. 9 is another side view of the loading unit of FIGS. 5-8.

Referring now to FIGS. 5 and 6, a closing mechanism 240 for approximating clamp 230 is shown. Closing mechanism 240 includes a pin 242 and an angled slot 244. Pin 242 is disposed on a clamp link of DLU 200*a* or surgical instrument 100 (not part of clamp 230). Slot 244 is shown disposed on first portion 232 of clamp 230. As can be appreciated with reference to FIGS. 5 and 6, actuation of clamp 230 utilizing lever 140 moves articulation link of surgical instrument 100. The articulation link is connected to clamp link when DLU 200*a* is connected to instrument 100. Movement of the clamp link causes relative movement between pin 242 and slot 244. That is, proximal movement of pin 242 relative to slot 244 causes first portion 232 of clamp 230 to move (e.g., cam, pivot, etc.) towards second portion 234 of clamp 230. Any suitable structure may be incorporated with surgical instrument 100 and/or DLU 200*a* to cause the relative movement between pin 242 and slot 244. For example, surgical instrument 100 may include a clamp collar that is longitudinally movable upon actuation of a movable handle/knob/etc. In such an embodiment, distal translation of clamp collar may cam first portion 232 relative to second portion 234, and thus to approximate clamp 230. Additionally, proximal translation of clamp collar may open clamp 230. Additionally, as shown in FIGS. 2-4, closing mechanism 240 may be contained (or at least partially contained) within a housing 246, e.g., to help prevent undesired pinching of tissue.

Additionally, with reference back to FIG. 2, an embodiment of the present disclosure includes a tab 250 disposed on clamp 230. (In FIG. 2, for example, tab 250 is shown on second portion 234 of clamp.) It is envisioned that tab 250 is configured to mate with an aperture 251 (shown in phantom in FIG. 2) disposed on the opposite portion of the clamp 230 (e.g., the first portion 232) when clamp 230 is in a closed position. This tab 250/aperture combination may help maintain clamp 230 in a closed position and may also help maintain alignment of the portions 232, 234 of clamp 230 during use.

In a further embodiment, the jaw members and/or clamp are pivotally connected to the proximal portion 210 of the DLU. The DLU includes the clamp link and an articulation link, each of which engage a corresponding link in the elongated portion of the surgical instrument 100 upon engaging the DLU with the elongated portion. The handle portion of the instrument 100 includes any combination of levers, slides, buttons, pivotable handles, etc., for separately actuating the jaw members, clamp and pivoting (also known as articulation) of the jaw members and/or clamp with respect to the proximal portion 210 and elongated portion of the surgical instrument. An articulating loading unit for an endoscopic surgical stapler is disclosed in U.S. Pat. No. 6,953,139 to Milliman et al., the entire contents of which are hereby incorporated by reference herein, in its entirety.

The present disclosure also relates to a method of using the described surgical instrument 100 and DLU 200*a*. The method, as described above, includes providing surgical instrument 100, clamping tissue via clamp 230, approximating jaw members 220, firing staples (e.g., sequentially) or delivering energy to the tissue, and/or cutting tissue (e.g., with a knife disposed in mechanical cooperation with DLU 200*a* or surgical instrument 100, or using a separate instrument). In certain embodiments, clamp 230 is actuated, clamping onto intestinal tissue. Then, the interior of the intestinal tissue is washed out or otherwise cleansed. The tissue is then cut and stapled or joined using electrosurgical energy. In this way, the interior intestinal tissue is cleansed up to the location of the clamp, including the area where the jaws will engage the intestinal tissue to be stapled and/or cut, once the jaws are approximated.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical stapling instrument for surgically joining tissue, comprising:
   a handle portion;
   an endoscopic portion extending distally from the handle portion and defining a first longitudinal axis;
   a pair of jaw members disposed adjacent a distal end of the endoscopic portion and extending generally distally therefrom, at least one of the jaw members being movable with respect to the other between an open position and an approximated position for engaging body tissue therebetween, the pair of jaw members comprising an anvil assembly and a cartridge assembly, the cartridge assembly housing a plurality of surgical staples arranged to be ejected in a direction transverse to the first longitudinal axis and toward the anvil assembly; and
   a clamp disposed adjacent the jaw members and extending generally distally from the endoscopic portion, the clamp being movable between an open position and an approximated position for engaging body tissue, and wherein the clamp is independently movable with respect to the jaw members.

2. The surgical instrument of claim 1, wherein the clamp includes a first portion and a second portion, and wherein at least one portion of the clamp is pivotable with respect to the other portion about a pivot point disposed at a proximal portion of the clamp.

3. The surgical instrument of claim 1, wherein each of the pair of jaw members is substantially parallel to the clamp.

4. The surgical instrument of claim 1, wherein the pair of jaw members extends linearly along the first longitudinal axis.

5. The surgical instrument of claim 1, wherein the pair of jaw members are configured to deliver electrosurgical energy to tissue.

6. The surgical instrument of claim 1, wherein the pair of jaw members are curved with respect to the first longitudinal axis.

7. The surgical instrument of claim 6, wherein the clamp is curved with respect to the first longitudinal axis.

8. The surgical instrument of claim 7, wherein the clamp is disposed alongside a concave side of the pair of jaws.

9. The surgical instrument of claim 1, wherein the jaw members are part of a loading unit, the loading unit being attachable to the endoscopic portion.

10. The surgical instrument of claim 1, wherein the pair of jaw members are rotatable with respect to the handle portion.

11. The surgical instrument of claim 1, wherein the pair of jaw members defines a second longitudinal axis, the pair of jaw members being movable from a first position where the second longitudinal axis is substantially aligned with the first longitudinal axis to at least a second position where the second longitudinal axis is disposed at an angle to the first longitudinal axis.

12. A loading unit configured for releasable engagement with a surgical instrument, the loading unit comprising:
    a body portion defining a first longitudinal axis, a proximal portion of the body portion configured for releasable engagement with an endoscopic portion of the surgical instrument;
    a pair of jaw members disposed distally of the body portion, at least one of the jaw members being movable with respect to the other between an open position and an approximated position for engaging body tissue therebetween, the pair of jaw members comprising an anvil assembly and a cartridge assembly, the cartridge assembly housing a plurality of surgical staples arranged to be ejected in a direction transverse to the longitudinal axis and toward the anvil assembly; and
    a clamp disposed adjacent the jaw members, the clamp being movable between an open position and an approximated position for engaging body tissue, and wherein the clamp is independently movable with respect to the jaw members.

13. The loading unit of claim 12, wherein the clamp includes a first portion and a second portion, and wherein at least one portion of the clamp is pivotable with respect to the other portion about a pivot point disposed at a proximal portion of the clamp.

14. The loading unit of claim 12, wherein each of the pair of jaw members is substantially parallel to the clamp.

15. The loading unit of claim 12, wherein the pair of jaw members extends linearly along the first longitudinal axis.

16. The loading unit of claim 12, wherein the pair of jaw members are configured to deliver electrosurgical energy to tissue.

17. The loading unit of claim 12, wherein the pair of jaw members are curved with respect to the first longitudinal axis.

18. The loading unit of claim 17, wherein the clamp is curved with respect to the first longitudinal axis.

19. The loading unit of claim 18, wherein the clamp is disposed alongside a concave side of the pair of jaws.

* * * * *